(12) United States Patent
Kim et al.

(10) Patent No.: US 12,168,125 B2
(45) Date of Patent: Dec. 17, 2024

(54) BEAUTY EQUIPMENT

(71) Applicant: LG ELECTRONICS INC., Seoul (KR)

(72) Inventors: Woohyun Kim, Seoul (KR); Hyoungjun Kim, Seoul (KR); Yonggeun Jin, Seoul (KR)

(73) Assignee: LG ELECTRONICS INC., Seoul (KR)

( * ) Notice: Subject to any disclaimer, the term of this patent is extended or adjusted under 35 U.S.C. 154(b) by 0 days.

(21) Appl. No.: 18/569,527

(22) PCT Filed: Jul. 8, 2021

(86) PCT No.: PCT/KR2021/008725
§ 371 (c)(1),
(2) Date: Dec. 12, 2023

(87) PCT Pub. No.: WO2022/270666
PCT Pub. Date: Dec. 29, 2022

(65) Prior Publication Data
US 2024/0261569 A1 Aug. 8, 2024

(30) Foreign Application Priority Data
Jun. 25, 2021 (KR) .................. 10-2021-0083440

(51) Int. Cl.
*A61N 1/32* (2006.01)
*A61F 7/00* (2006.01)
(Continued)

(52) U.S. Cl.
CPC ............. *A61N 1/327* (2013.01); *A61F 7/007* (2013.01); *A61N 1/044* (2013.01); *A61N 1/0472* (2013.01);
(Continued)

(58) Field of Classification Search
CPC .................. A61N 1/328; A61N 5/0616; A61N 2007/0034
See application file for complete search history.

(56) References Cited

U.S. PATENT DOCUMENTS

| 10,376,693 B2 | 8/2019 | Yamazaki |
| 2016/0121108 A1* | 5/2016 | Kondo ............... A61B 18/1402 601/2 |

FOREIGN PATENT DOCUMENTS

| JP | 2011-041706 | 3/2011 |
| JP | 2017-012513 | 1/2017 |

(Continued)

OTHER PUBLICATIONS

PCT International Application No. PCT/KR2021/008725, International Search Report dated Apr. 20, 2022, 4 pages.

*Primary Examiner* — George R Evanisko
(74) *Attorney, Agent, or Firm* — LEE, HONG, DEGERMAN, KANG & WAIMEY

(57) ABSTRACT

The present embodiment comprises: an ultrasonic transducer for generating ultrasonic waves; an inner electrode having a space in which the ultrasonic transducer is accommodated; a window disposed outside the outer periphery of the inner electrode; an LED PCB disposed at the rear of the window and having an LED disposed thereon; and an outer electrode spaced apart from the inner electrode on the window, wherein the inner electrode comprises: a front body having the ultrasonic transducer disposed on the rear surface thereof; and a hollow body protruding backward from the outer periphery of the front body and having a space formed therein, wherein an inner waterproofing ring is disposed between the hollow body and the window.

9 Claims, 11 Drawing Sheets

(51) Int. Cl.
    *A61N 1/04*          (2006.01)
    *A61N 1/06*          (2006.01)
    *A61N 1/20*          (2006.01)
    *A61N 1/30*          (2006.01)
    *A61N 1/36*          (2006.01)
    *A61N 7/02*          (2006.01)

(52) U.S. Cl.
    CPC ............... *A61N 1/06* (2013.01); *A61N 1/205* (2013.01); *A61N 1/303* (2013.01); *A61N 1/36014* (2013.01); *A61N 7/02* (2013.01); *A61F 2007/0003* (2013.01); *A61F 2007/0004* (2013.01); *A61F 2007/0071* (2013.01); *A61N 2007/025* (2013.01)

(56) References Cited

FOREIGN PATENT DOCUMENTS

| | | |
|---|---|---|
| KR | 10-2014-0079602 | 6/2014 |
| KR | 10-2016-0060943 | 5/2016 |
| KR | 10-2016-0079396 | 7/2016 |
| KR | 10-2017-0074724 | 6/2017 |
| KR | 10-2017-0098577 | 8/2017 |
| KR | 10-1773508 | 9/2017 |
| KR | 10-2265180 | 6/2021 |

* cited by examiner

[FIG. 1]
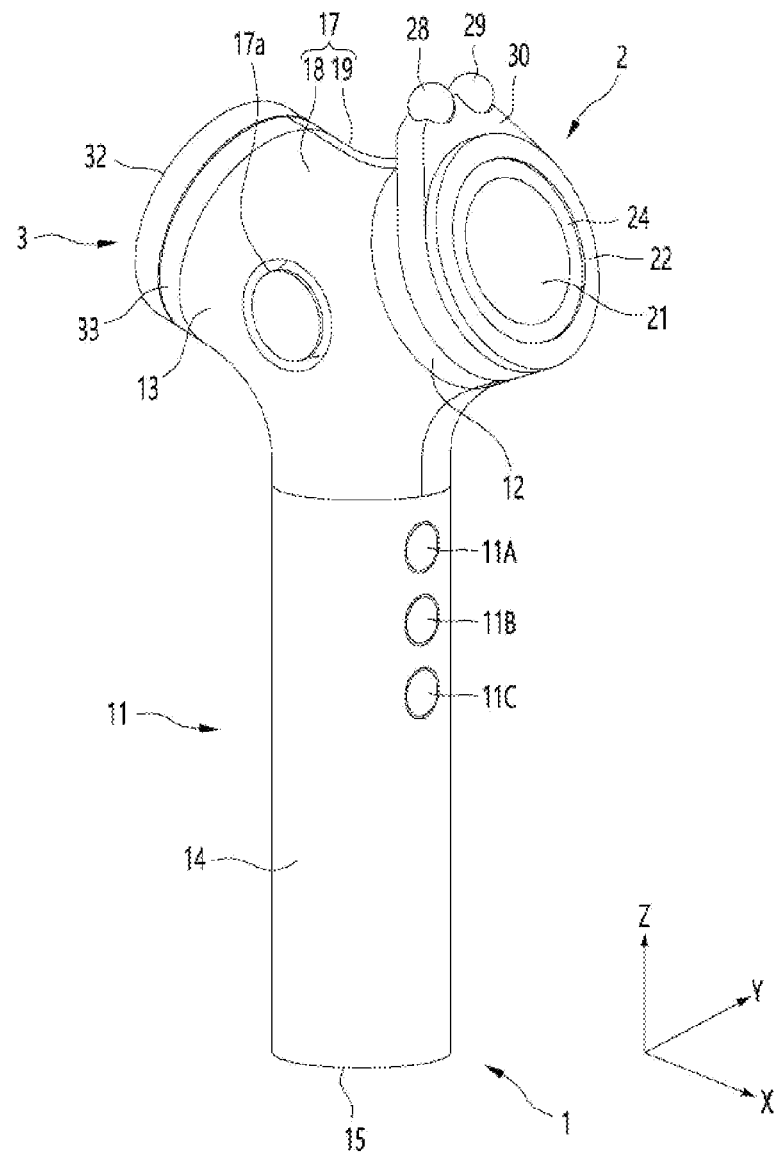

[FIG. 2]
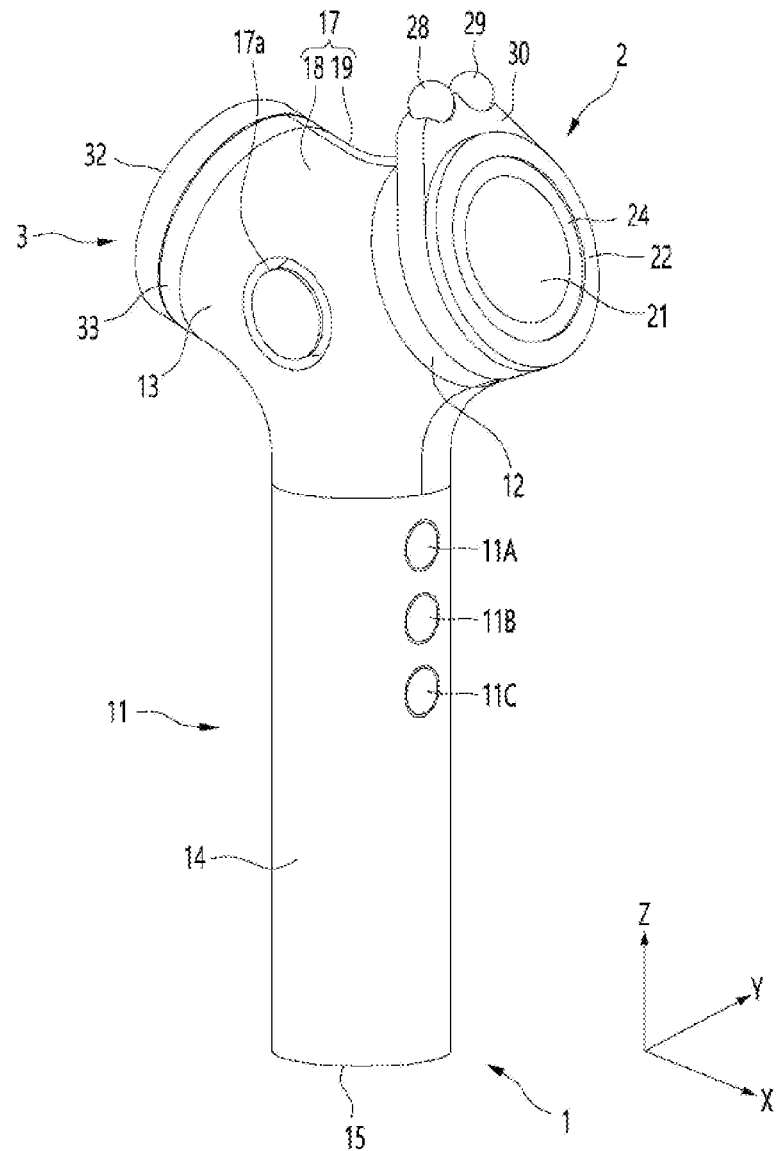

[FIG. 3]
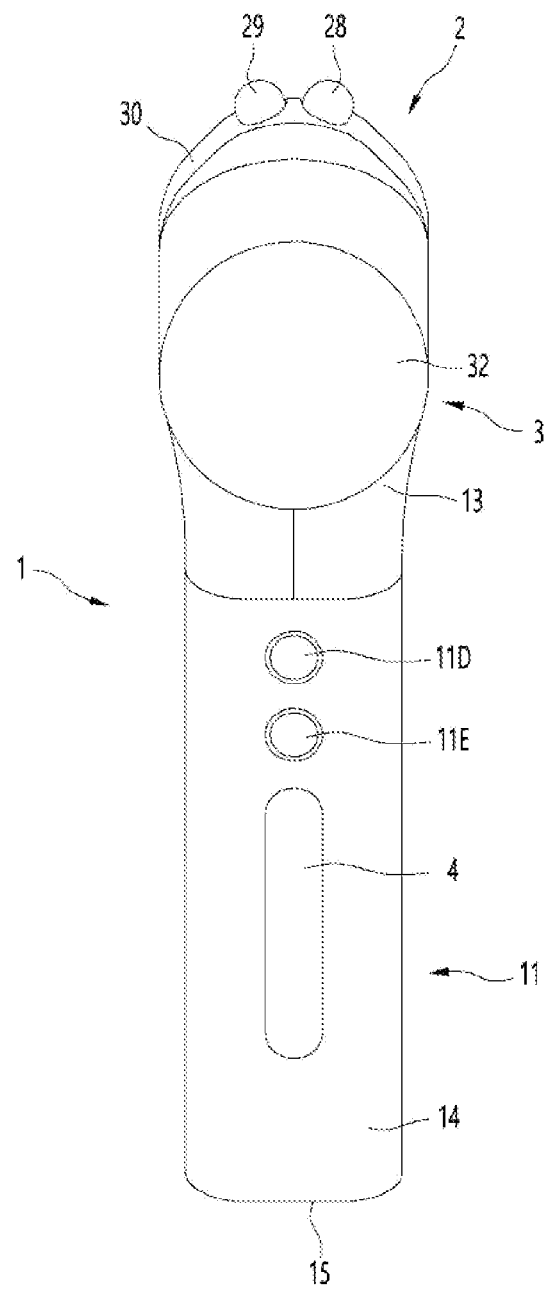

[FIG. 4]
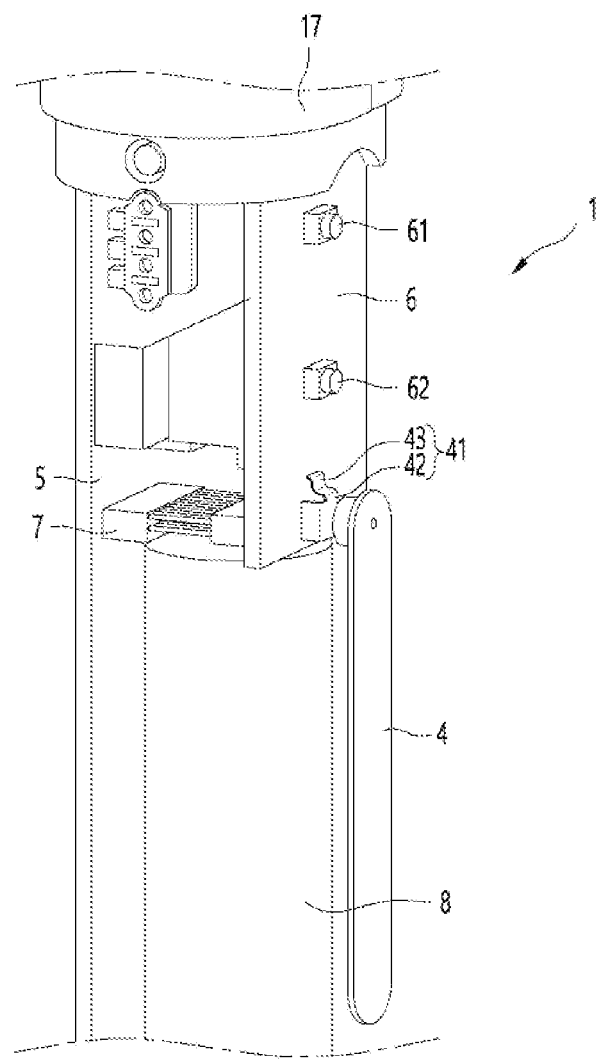

[FIG. 5]
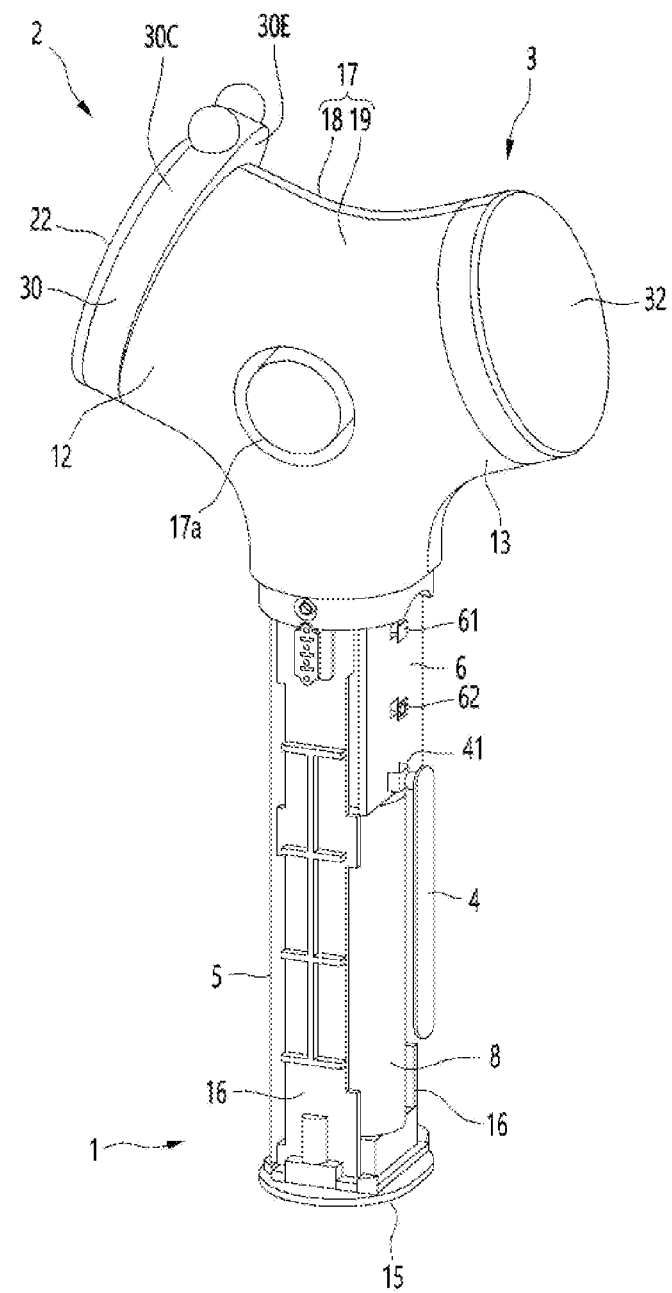

[FIG. 6]
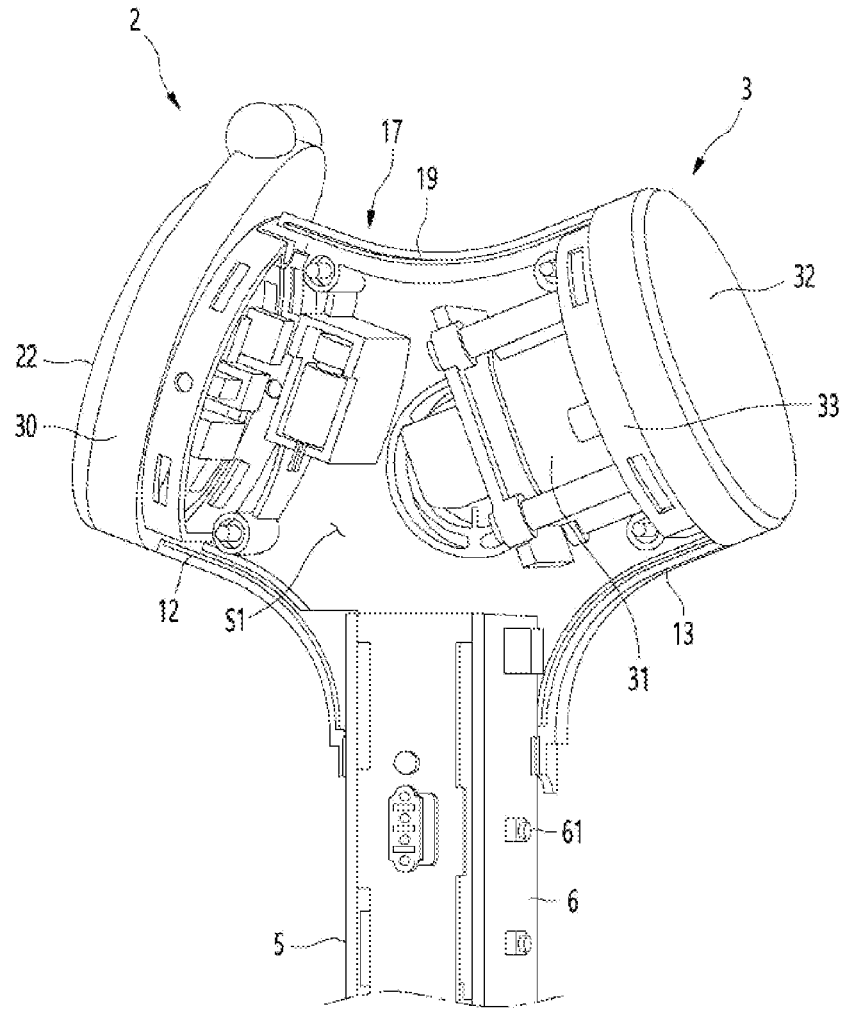

[FIG. 7]
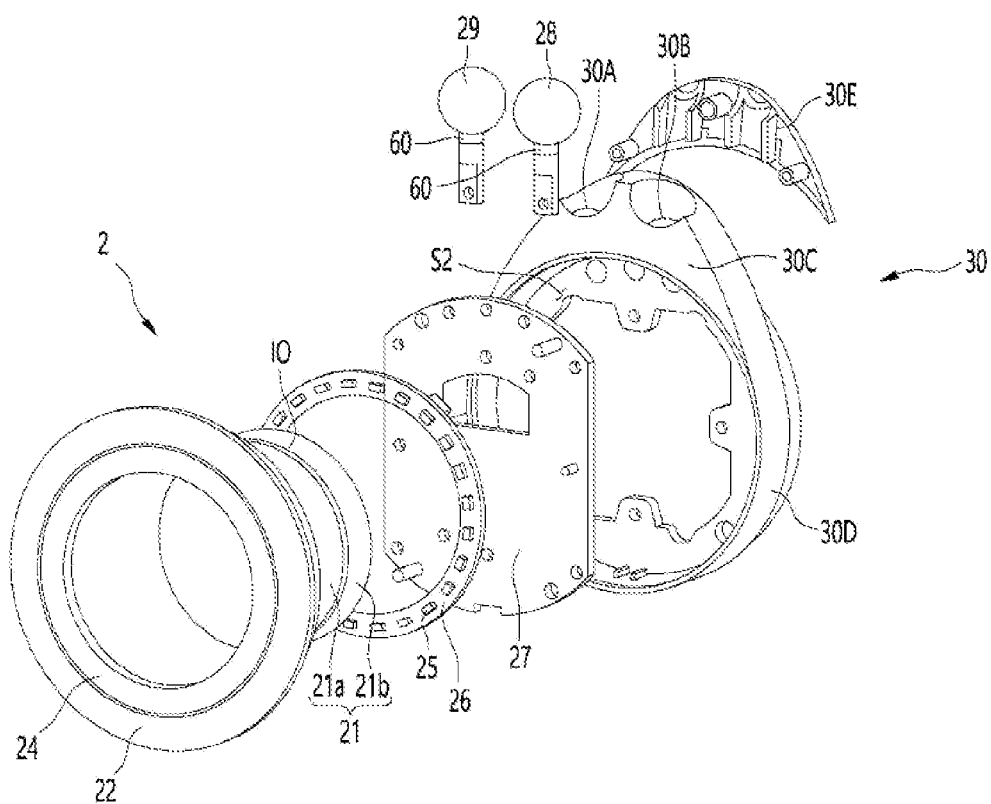

[FIG. 8]
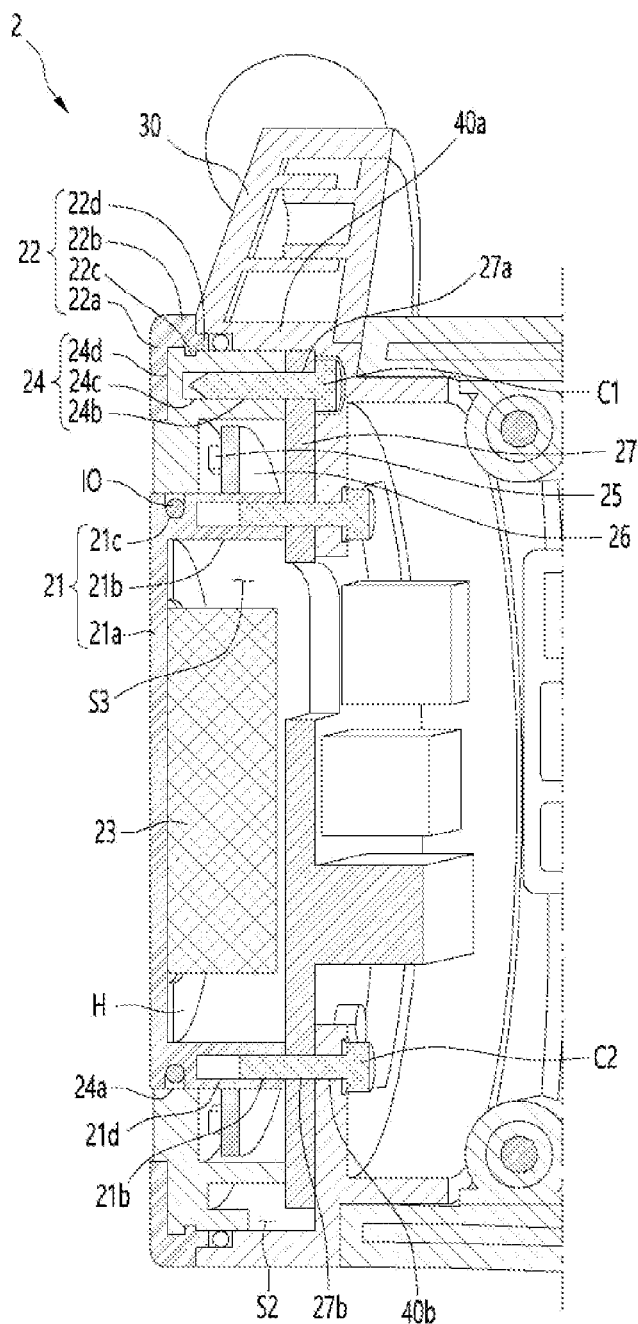

[FIG. 9]
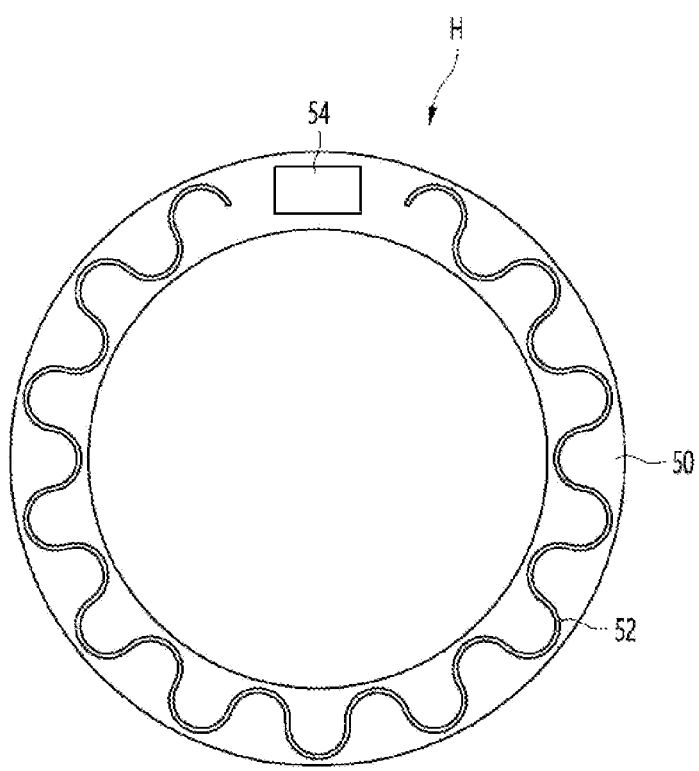

[FIG. 10]
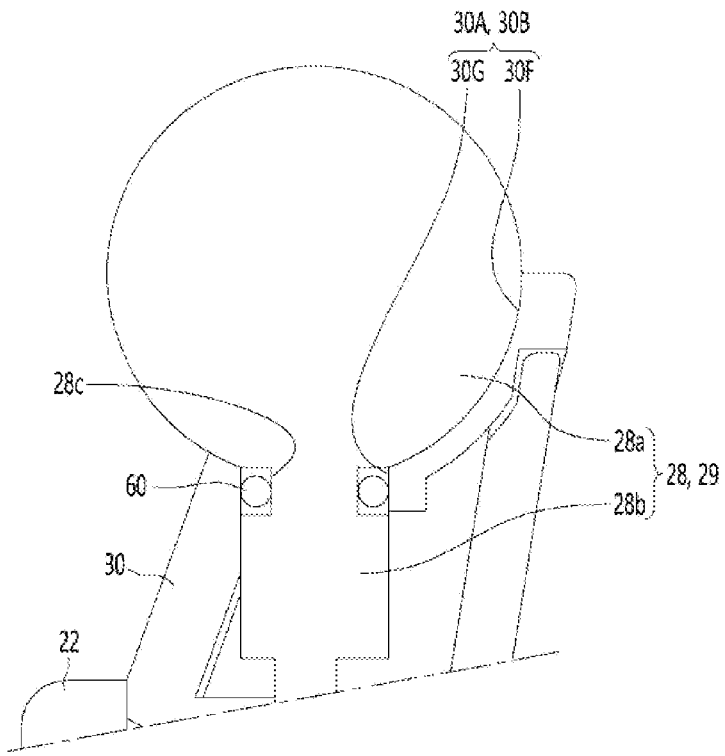
[FIG. 11]
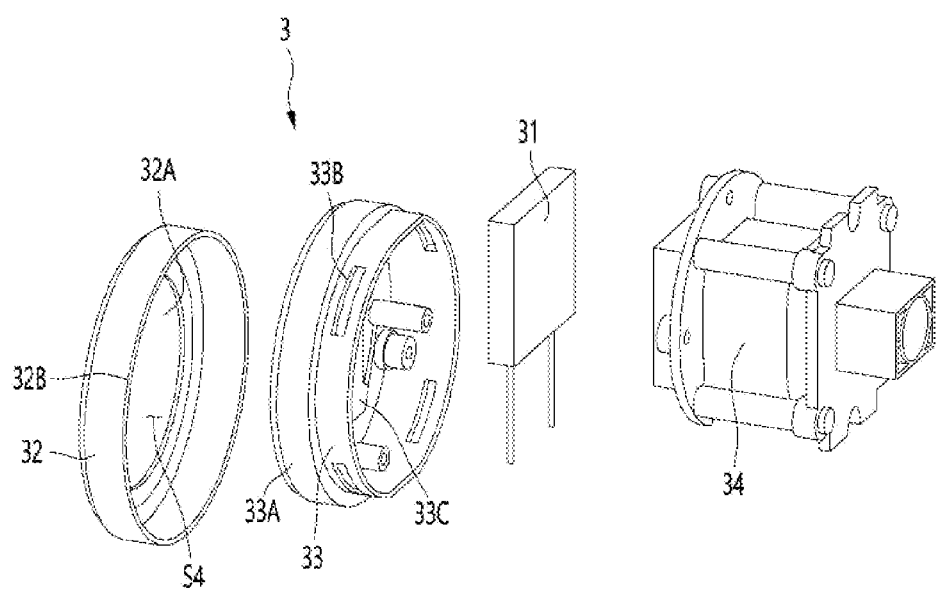

[FIG. 12]
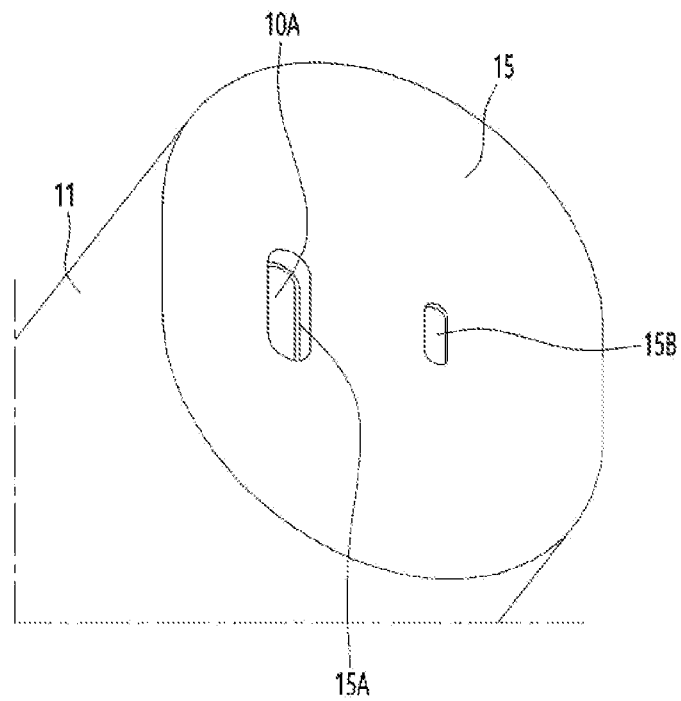

BEAUTY EQUIPMENT

CROSS-REFERENCE TO RELATED APPLICATION(S)

This application is the National Stage filing under 35 U.S.C. 371 of International Application No. PCT/KR2021/008725, filed on Jul. 8, 2021, which claims the benefit of earlier filing date and right of priority to Korean Application No. 10-2021-0083440, filed on Jun. 25, 2021, the contents of which are all hereby incorporated by reference herein in their entireties.

TECHNICAL FIELD

The present disclosure relates to beauty equipment.

BACKGROUND ART

In general, to penetrate effective ingredients of cosmetics deep into the skin and provide nutrition to the skin, cosmetic methods such as tapping or rubbing the effective ingredients of cosmetics applied to the skin by hand are used. Recently, a galvanic ion introduction function or an ultrasonic function has been used or massagers with hot and cold functions have been used.

An example of a conventional massager is a complex beauty device disclosed in Korean Patent Publication No. KR 10-2017-0098577 A1 (published on Aug. 30, 2017).

The complex beauty device comprises a base body provided with a plurality of ventilation holes, a main body detachably coupled to the upper cover and having a head configured to supply ions in contact with the skin of a user, a thermoelectric element unit coupled to the main body and configured to emit hot or cold heat to the skin through the head, a heat dissipation unit provided on the base body and configured to dissipate heat from the thermoelectric element unit by introducing external air through the plurality of ventilation holes, an ultrasonic generator provided on the head to generate ultrasonic waves, and a vibration unit provided on the upper cover to vibrate the head.

DISCLOSURE

Technical Problem

An object of the present disclosure is to provide a beauty equipment for minimizing penetration of moisture.

Technical Solution

In an aspect of the present disclosure, beauty equipment comprises an ultrasonic vibrator configured to generate ultrasonic waves, an inner electrode with a space in which the ultrasonic vibrator is accommodated, a window disposed outside an outer circumference of the inner electrode, a light emitting diode (LED) printed circuit board (PCB) disposed behind the window and having an LED disposed thereon, and an outer electrode spaced apart from the inner electrode on the window.

The inner electrode may comprise a front body having a rear surface on which the ultrasonic vibrator is disposed, and a hollow body protruding rearward from an outer circumference of the front body and having the space formed therein.

An inner waterproof ring may be disposed between the hollow body and the window.

A groove facing the window may be formed on an outer circumference of the hollow body.

The inner waterproof ring may be accommodated in the groove.

The beauty equipment may further comprise a heater disposed on a rear surface of the front body.

The heater may further comprise a film, a heating element formed on the film, and a temperature sensor disposed on the film.

The window may comprise a rear protrusion surrounding the outer circumference of the hollow body.

The LED PCB may be accommodated between the hollow body and the rear protrusion.

The beauty equipment may further comprise a front cover, and the front cover is formed with an electrode coupler to which the inner electrode is coupled; and a window receiving portion that accommodates a portion of the window.

An outer waterproof ring may be disposed between the window receiving portion and the window.

The outer electrode comprises a rear protrusion inserted between the window receiving portion and the window and disposed in front of the outer waterproof ring.

The beauty equipment may further comprise a head PCB to which each of the inner electrode and the outer electrode is connected, and an eye care member connected to the head PCB.

The beauty equipment may further comprise a front cover with a through portion through which the eye care member passes.

The eye care member may comprise an eye care waterproof ring disposed thereon and configured to seal a space between the through portion and the eye care member.

The eye care member may comprise a ball exposed outside the front cover, and a terminal protruding from the ball and passing through the through portion.

The eye care waterproof ring may be accommodated in a groove formed in the terminal and may be in contact with the through portion.

Advantageous Effects

According to an embodiment of the present disclosure, an inner waterproof ring may seal a space between a hollow body of an inner electrode and a window, thereby minimizing penetration of moisture through the space between the inner electrode and the window.

A groove formed on an outer circumference surface of the hollow body of the inner waterproof ring is accommodated, and thus the inner waterproof ring may be hidden between the inner electrode and the window, and the overall appearance may be simple.

A heater disposed on a rear surface of a front body may raise a temperature of the front body, thereby minimizing contact of a cold front body with the skin of a user.

A rear protrusion of the window may protect a hollow body of the inner electrode and a light emitting diode (LED) printed circuit board (PCB).

The LED PCB may be accommodated between the hollow body and the rear protrusion, and thus the beauty equipment may be as compact as possible.

An outer waterproof ring seals a space between a window receiving portion of a front cover and the window, thereby minimizing penetration of moisture through the space between the front cover and the window.

The rear protrusion of the outer electrode may maintain an outer waterproof ring in place between the window receiving portion and the window and may limit arbitrary removal of the outer waterproof ring.

The rear protrusion of the outer electrode covers the outer waterproof ring, and thus the overall appearance is simple.

The eye care waterproof ring may seal a space between the eye care member and the front cover, thereby minimizing moisture from penetrating between the eye care member and the front cover.

The eye care waterproof ring is hidden in the front cover, and the overall appearance may be simple.

DESCRIPTION OF DRAWINGS

FIG. 1 is a perspective view of beauty equipment according to the present embodiment.

FIG. 2 is a front view of the beauty equipment according to the present embodiment.

FIG. 3 is a bottom view of the beauty equipment according to the present embodiment.

FIG. 4 is a diagram showing a lower housing separated from the beauty equipment according to the present embodiment.

FIG. 5 is a diagram showing a main printed circuit board (PCB) and a sub-PCB, according to the present embodiment.

FIG. 6 is a diagram showing a head housing separated from the beauty equipment according to the present embodiment.

FIG. 7 is an exploded perspective view of a front assembly according to the present embodiment.

FIG. 8 is a cross-sectional view of the front assembly according to the present embodiment.

FIG. 9 is a front view of a heater according to the present embodiment.

FIG. 10 is a cross-sectional view of an eye care member according to the embodiment.

FIG. 11 is an exploded perspective view of a rear assembly according to the present embodiment.

FIG. 12 is a diagram showing a base according to the present embodiment.

BEST MODE

Hereinafter, detailed embodiments of the present disclosure will be described in detail with reference to the accompanying drawings.

Reference will now be made in detail to the exemplary embodiments of the present disclosure, examples of which are illustrated in the accompanying drawings. The suffixes "module" and "unit" of elements herein are used for convenience of description and thus can be used interchangeably and do not have any distinguishable meanings or functions.

In the following description of the at least one embodiment, a detailed description of known functions and configurations incorporated herein will be omitted for the purpose of clarity and for brevity. The features of the present disclosure will be more clearly understood from the accompanying drawings and should not be limited by the accompanying drawings, and it is to be appreciated that all changes, equivalents, and substitutes that do not depart from the spirit and technical scope of the present disclosure are encompassed in the present disclosure.

It will be understood that, although the terms first, second, third etc. may be used herein to describe various elements, these elements should not be limited by these terms. These terms are only used to distinguish one element from another element.

It will be understood that when an element is referred to as being "connected to" or "disposed on" another element, it may be directly on, connected to or disposed on the other element or intervening elements may be present.

The singular expressions in the present specification comprise the plural expressions unless clearly specified otherwise in context.

It will be further understood that the terms "comprises" and/or "comprising" when used in this specification, specify the presence of stated features, integers, steps, operations, elements, components, or combinations thereof, but do not preclude the presence or addition of one or more other features, integers, steps, operations, elements, components, or combinations thereof.

FIG. 1 is a perspective view of beauty equipment according to the present embodiment. FIG. 2 is a front view of the beauty equipment according to the present embodiment. FIG. 3 is a bottom view of the beauty equipment according to the present embodiment. FIG. 4 is a diagram showing a lower housing separated from the beauty equipment according to the present embodiment. FIG. 5 is a diagram showing a main printed circuit board (PCB) and a sub-PCB, according to the present embodiment. FIG. 6 is a diagram showing a head housing separated from the beauty equipment according to the present embodiment.

As shown in FIGS. 1 to 3, the beauty equipment may comprise a main body 1, a front assembly 2, and a rear assembly 3.

The main body 1 may comprise a handle 11 and a pair of protrusions 12 and 13 protruding from an upper portion of the handle 11.

The handle 11 may be formed to be long in an up-and-down direction Z. An accommodation space that accommodates a main PCB 5, a sub-PCB 6, a battery 8, and the like therein may be formed inside the handle 11.

The handle 11 may be formed by a lower housing 14, and the accommodation space may be formed inside the lower housing 14. The lower housing 14 may be a hollow body that is long in the up-and-down direction Z and has an accommodation space formed therein.

The handle 11 may comprise a base 15 that defines an appearance of a bottom surface of the beauty equipment. The base 15 may be coupled to a lower portion of the lower housing 14. The base 15 may block the accommodation space of the lower housing 14 below the lower housing 14.

The handle 11 may further comprise a PCB mounter 16 for mounting and supporting the main PCB 5 and the sub-PCB 6.

The PCB mounter 16 may be coupled to the base 15 and define a framework of the handle 11. The PCB mounter 16 may be placed inside the lower housing 14.

The PCB mounter 16 may be formed to be long in the up-and-down direction Z. A lower portion of the PCB mounter 16 may be coupled to the base 15, and an upper portion of the PCB mounter 16 may be coupled to a head housing 17 to be described below.

The PCB mounter 16 may be placed in plural numbers on the base 15.

The plurality of PCB mounters 16 may comprise a pair of PCB mounters spaced apart in the left and right directions, and the pair of PCB mounters may comprise a left mounter and a right mounter.

A first protrusion 12 and a second protrusion 13, which constitute the pair of protrusions 12 and 13, may protrude in different directions.

The front assembly 2 may be placed in the first protrusion 12, and the first protrusion 12 may be a front coupler to which the front assembly 2 is coupled.

The first protrusion 12 may have an obtuse inclination angle with the handle 11. The first protrusion 12 may be defined as protruding obliquely from an upper side of the handle 11 toward an upper front side. The first protrusion 12 may have a hollow shape and may be connected to the inside of the handle 11.

The rear assembly 3 may be placed in the second protrusion 13, and the second protrusion 13 may be a rear coupler to which the rear assembly 3 is coupled.

The second protrusion 13 may have an obtuse inclination angle with each of the handle 11 and the first protrusion 12. The second protrusion 13 may have a hollow shape. The second protrusion 13 may be defined as protruding obliquely from the upper side of the handle 11 toward an upper rear side. The second protrusion 13 may have a hollow shape and may be connected to the inside of the handle 11.

The first protrusion 12 and the second protrusion 13 may be formed by the head housing 17.

The head housing 17 may be formed in an approximately 'Y' shape, a lower portion of the head housing 17 may form the handle 11 together with the lower housing 14, and an upper portion of the head housing 17 may be divided into two branches to form the first protrusion 12 and the second protrusion 13.

The head housing 17 may have a hollow shape. The head housing 17 may be configured by a combination of a plurality of side housings 18 and 19. The plurality of side head housings may comprise a left head housing 18 and a right head housing 19.

A space S1 (refer to FIG. 6) may be formed inside the head housing 17 to accommodate a portion of the front assembly 2 and a portion of the rear assembly 3.

A ventilation hole 17a may be formed in the head housing 17 to dissipate heat from the thermoelectric element 31 and the heat sink 34, to be described below, to the outside. The ventilation hole 17a may be formed in each of the left head housing 18 and the right head housing 19.

The front assembly 2 may be placed at the first protrusion 12. A portion of the front assembly 2 may be accommodated in a space S1 and the other portion of the front assembly 2 may be exposed to the outside.

The rear assembly 3 may be placed at the second protrusion 13. A portion of the rear assembly 3 may be accommodated in the space S1 and the other portion of the rear assembly 3 may be exposed to the outside.

The beauty equipment may further comprise an iontophoresis electrode 4.

As shown in FIG. 3, the iontophoresis electrode 4 may be disposed on an outer surface of the main body 1. The iontophoresis electrode 4 may be disposed on a rear surface of the handle 11.

The iontophoresis electrode 4 may be spaced apart from the front assembly 2 and the rear assembly 3. The iontophoresis electrode 4 may be disposed on the lower housing 14 such that one surface of the iontophoresis electrode 4 is exposed to the outside. When a user holds the handle 11, the hand of the user may be in contact with the iontophoresis electrode 4.

The iontophoresis electrode 4 may be a plate formed to be long in the up-and-down direction Z.

As shown in FIGS. 5 and 6, the iontophoresis electrode 4 may be connected to the main PCB 5 or a server PCB 6 through a connection portion 41.

When the main PCB 5 is larger than the server PCB 6, the iontophoresis electrode 4 may be connected to the sub-PCB 6.

As shown in FIG. 5, the connection portion 41 may comprise a connection piece 42 disposed between the sub-PCB 6 and the iontophoresis electrode 4.

The connection piece 42 may protrude from a rear surface of the sub-PCB 6.

The connection portion 41 may comprise a spring 43 disposed on the connection piece 42. The spring 43 may elastically support the connection piece 42 when pressed against the connection piece 42, and when the external force applied to the connection piece 42 is removed, the connection piece 42 may be pressurized in a rearward direction. An example of the spring 43 may be a leaf spring that is bent at least once.

As shown in FIGS. 4 to 6, the beauty equipment may comprise the main PCB 5 and the sub-PCB 6.

An input unit for inputting an intensive care mode may be disposed on the main PCB 5.

The input unit disposed on the main PCB 5 may comprise a plurality of switches for an intensive care mode and an eye care mode.

The plurality of switches may be arranged in a row and spaced apart in the up-and-down direction on a front surface of the main PCB 5.

The plurality of switches may comprise a power switch for the intensive care mode and the eye care mode, a mode selection switch for selecting of the intensive care mode and the eye care mode, and a level switch for selecting a care level (output intensity).

As shown in FIGS. 1 and 2, on a front surface of the handle 11, a power button 11A for switching on or off the power switch, a mode selection button 11B for switching on or off the mode selection switch, and a level button 11C for switching on or off the level switch.

The main PCB 5 may be equipped with a high frequency generator circuit and a microcurrent generator circuit. The main PCB 5 may be equipped with an iontophoresis generator circuit.

The main PCB 5 may be equipped with a power terminal circuit, a battery charging circuit, and a main CPU circuit.

The main PCB 5 may be placed inside the main body 1, particularly inside the lower housing 14, and a portion of an upper portion of the main PCB 5 may be inserted into the head housing 17.

The main PCB 5 may mainly control the front assembly 2 and may be placed closer to the front assembly 2 among the front assembly 2 and the rear assembly 3.

The main PCB 5 may be placed closer to the first protrusion 12 among the first protrusion 12 and the second protrusion 13.

An input unit 61 that inputs a cooling care mode may be disposed on the sub-PCB 6. The input unit 61 may be a cooling care power switch such as a tact switch placed on the rear surface of the sub-PCB 6.

The sub-PCB 6 may comprise a cooling care controller 62 for adjusting the intensity of the cooling care mode. The cooling care controller 62 may be disposed on the rear surface of the sub-PCB 6 and may be a level selection switch such as a tact switch for selecting the cooling care level (temperature).

As shown in FIG. 3, on the rear surface of the handle 11, a cooling mode button 11D for switching on or off a cooling care power switch and a level selection button 11E for switching on or off a level selection switch may be disposed.

The cooling mode button 11D and the level selection button 11E may be spaced apart from the iontophoresis electrode 4 in the up-and-down direction Z and may be placed at a higher position than the position of the iontophoresis electrode 4.

The user may input the cooling mode button 11D to input a cooling mode.

The user may input the level selection button 11E to adjust the intensity of the cooling mode.

The sub-PCB 6 may be equipped with an ultrasonic waves generator circuit.

The sub-PCB 6 may be equipped with an iontophoresis connection circuit.

The sub-PCB 6 may be placed inside the main body 1, particularly inside the lower housing 14, and a portion of an upper portion of the sub-PCB 6 may be inserted into the head housing 17.

The sub-PCB 6 may have a smaller size than the main PCB 5. The sub-PCB 6 may be disposed in parallel to the main PCB 5.

The sub-PCB 6 may be connected to the main PCB 5 through a connector 7.

An example of the connector 7 may be a board-to-board connector.

The connector 7 may be disposed between the main PCB 5 and the sub-PCB 6 and may be protected by the main PCB 5 and the sub-PCB 6.

The connector 7 may be disposed between a rear surface of the main PCB 5 and a front surface of the sub-PCB 6.

The connector 7 may connect a lower portion of the sub-PCB 6 to an upper or central portion of the main PCB 5.

The sub-PCB 6 may control the rear assembly 3 when the user manipulates the input unit 61 or the cooling care controller 62, and the sub-PCB 6 may be placed closer to the rear assembly 3 among the front assembly 2 and the rear assembly 3.

The sub-PCB 6 may be placed closer to the second protrusion 13 among the first protrusion 12 and the second protrusion 13.

According to the present embodiment, the power button 11A, the mode selection button 11B, and the level button 11C may be disposed on the front surface of the handle 11, the cooling mode button 11D and the level selection button 11E may be disposed on the rear surface of the handle 11, and a plurality of buttons 11A, 11B, 11C, 11D, and 11E for manipulation/input of the beauty equipment may be distributed and arranged on the front surface and rear surface of the handle 11.

When the plurality of buttons 11A, 11B, 11C, 11D, and 11E are distributed and arranged on the front surface and rear surface of the handle 11, the plurality of buttons 11A, 11B, 11C, 11D, and 11E may be separated from each other at a sufficient distance, and when any one of the plurality of buttons 11A, 11B, 11C, 11D, and 11E is pressed, pressing of other nearby buttons may be minimized.

When the power button 11A, the mode selection button 11B, and the level button 11C, which manipulate the front assembly 2, may be disposed on the front surface of the handle 11, and the cooling mode button 11D and the level selection button 11E, which manipulate the rear assembly 3, are disposed on the rear surface of the handle 11, the user is less likely to confuse the buttons while touching the front assembly 2 or the rear assembly 3 to their face.

As shown in FIG. 5, the battery 8 may be placed below the connector 7 and the sub-PCB 6. The battery 8 may be a power supply and may be DC Power, and the battery and the power supply are described using the same reference numerals.

FIG. 7 is an exploded perspective view of a front assembly according to the present embodiment. FIG. 8 is a cross-sectional view of the front assembly according to the present embodiment.

The front assembly 2 may be a front head located approximately at an upper front of the beauty equipment.

The front assembly 2 may comprise an inner electrode 21, an outer electrode 22, an ultrasonic vibrator 23, a window 24, a light emitting diode (LED) 25, and a light emitting diode (LED) printed circuit board (PCB) 26.

As shown in FIGS. 1, 2, and 8, the inner electrode 21 and the outer electrode 22 may be arrange to be exposed to the outside.

A space S3 in which the ultrasonic vibrator 23 is accommodated may be formed in the inner electrode 21. The inner electrode 21 may be formed in a three-dimensional shape.

The inner electrode 21 may be a SUS head made of a SUS material.

The inner electrode 21 may comprise a front body 21a and a hollow body 21b.

The front body 21a may be a body that comes into contact with the skin of the user when the user places the front assembly 2 on the face of the user.

The front body 21a may have a disk shape.

The rear surface of the front body 21a may face the inside of the hollow body 21b.

The hollow body 21b may protrude rearward from an outer circumference of the front body 21a. The hollow body 21b may have a hollow cylindrical shape with an empty interior. The space S3 in which the ultrasonic vibrator 23 is accommodated may be formed inside the hollow body 21b.

The inner electrode 21 may be an ultrasonic waves head that transmits ultrasonic waves generated by the ultrasonic vibrator 23 to the user.

The inner electrode 21 may be disposed inside the window 24, and an outer circumference surface of the hollow body 21b of the inner electrode 21 may face an inner circumference surface of the window 24 in a radial direction.

The front assembly 2 may further comprise a heater H.

The heater H may be placed on the inner electrode 21 to increase the temperature of the inner electrode 21. When the user touches the inner electrode 21 to the skin, if the inner electrode 21 is cold, the user may feel uncomfortable.

Before the user contacts the inner electrode 21 with the skin, the heater H may be turned on to heat the inner electrode 21.

The heater H may heat the inner electrode 21 inside the inner electrode 21. The heater H may be accommodated in the space S3 together with the ultrasonic vibrator 23.

The heater H may be placed close to a portion of the inner electrode 21, which is in contact with the skin of the skin, and the heater H may be placed on the rear surface of the front body 21a.

The rear surface of the front body 21a may comprise an ultrasonic vibrator area in which the ultrasonic vibrator 23 is disposed, and a heater placement area in which the heater H is disposed.

The heater H may be spaced apart from the ultrasonic vibrator 23, and the heater placement area may be placed outside the ultrasonic vibrator area.

For example, the heater H may be turned on when the beauty equipment is turned on and turned off when a setting temperature is reached. As another example of the heater H, when power of the beauty equipment may be input, if the user inputs a heater input unit provided in the input unit, the heater H may be turned on, and when the setting temperature is reached, the heater H may be turned off.

An inner waterproofing member IO may be disposed between the inner electrode 21 and the window 24 to prevent moisture and the like from penetrating between the inner electrode 21 and the window 24.

An example of the inner waterproofing member IO may be an inner waterproof ring formed in a ring shape. Hereinafter, the inner waterproof ring will be described by referring to reference numeral IO.

The inner waterproof ring IO may be disposed between the hollow body 21b and the window 24 and may seal a space between the hollow body 21b and the window 24.

The inner waterproof ring IO may be formed larger than the heater H. The inner waterproof ring IO may be arranged to be spaced apart from the heater H with the hollow body 21b disposed therebetween.

A groove 21c facing the window 24 may be formed on an outer circumference surface of the hollow body 21b. The groove 21c may be formed by depressing the outer circumference surface of the hollow body 21b. The groove 21c may be a receiving portion of an inner waterproof ring, in which the inner waterproof ring IO is accommodated.

The inner waterproof ring IO may be inserted into the groove 21c and accommodated, and the inner waterproof ring IO may be hidden in the hollow body 21b and not exposed to the front of the front assembly 2.

The outer electrode 22 may be disposed on the window 24 to be spaced apart from the inner electrode 21.

The outer electrode 22 may be disposed outside the inner electrode 21. The outer electrode 22 may be disposed to surround the inner electrode 21. An inner diameter of the outer electrode 22 may be greater than a diameter of the inner electrode 21. A ring-shaped gap may be formed between the inner electrode 21 and the outer electrode 22.

When the user touches the inner electrode 21 and the outer electrode 22 to the skin, especially the face, the inner electrode 21 and the outer electrode 22 may be electrically conductive.

The outer electrode 22 may be a high frequency composite head for generating a high frequency or microcurrent.

The outer electrode 22 may be formed in a three-dimensional shape and may comprise an outer front body 22a and an outer hollow body 22b.

The outer front body 22a may be shaped overall in a hollow disk shape.

The outer front body 22a may be arranged to be accommodated in a receiving portion 24d that is formed to be stepped against a front surface of the window 24. The outer front body 22a may be accommodated in the receiving portion 24d, and the front surface of the outer front body 22a may be aligned with the front surface of the window 24.

The outer hollow body 22b may protrude rearward from an outer circumference of the outer front body 22a. The outer hollow body 22b may be a hollow cylindrical shape with an empty interior.

A protrusion 22c that fits into a groove formed on the outer circumference surface of the window may be formed on an inner circumference surface of the outer hollow body 22b.

The ultrasonic vibrator 23 may be disposed inside the inner electrode 21 to generate ultrasonic waves. An example of the ultrasonic vibrator 23 may comprise a transducer of approximately 5.5 mm.

The ultrasonic vibrator 23 may be disposed on a rear surface of the front body 21a and may be accommodated in the space S3 to be protected by the inner electrode 21.

When the user touches the inner electrode 21 to the skin and the ultrasonic vibrator 23 operates, vibration by ultrasonic waves may be output through the inner electrode 21.

The inner electrode 21, the outer electrode 22, the ultrasonic vibrator 23, the iontophoresis electrode 4 (refer to FIGS. 3 to 5), the LED 25, and the heater H are used in various combinations to output a high frequency, microcurrent, ultrasonic waves, iontophoresis, LED light, and heat.

As an example of the beauty equipment, the inner electrode 21 may output iontophoresis, ultrasonic waves, a high frequency, microcurrent, or heat, and the high frequency or the microcurrent may be output to the outer electrode 22.

The iontophoresis may be output by the inner electrode 21 and the iontophoresis electrode 4.

The inner electrode 21 may have a negative (−) polarity, the iontophoresis electrode 4 may have a positive (+) polarity opposite thereto, and negative ions may be output from the inner electrode 21.

The negative ions output from the inner electrode 21 may push negative charges in cosmetics into the skin, and cosmetics may penetrate into the skin more quickly by the negative ions output from the inner electrode 21.

When the ultrasonic vibrator 23 is turned on, vibration by ultrasonic waves generated by the ultrasonic vibrator 23 may be output through the inner electrode 21.

Vibration by ultrasonic waves output through the inner electrode 21 may cause cracks in the skin and help cosmetics penetration.

The inner electrode 21 and the outer electrode 22 may selectively output a high frequency, positive (+) microcurrent, or negative (−) microcurrent.

The high frequency output from the inner electrode 21 and the outer electrode 22 may generate deep heat in the skin, and the microcurrent output from the inner electrode 21 and the outer electrode 22 may irritate the skin.

Electricity is conducted between the two electrodes 21 and 22, the inner electrode 21 and the outer electrode 22, and a high frequency or microcurrent flow is formed.

The window 24 may be disposed between the inner electrode 21 and the outer electrode 22. The window 24 may have a three-dimensional shape. The window 24 may be disposed outside the outer circumference of the inner electrode 21. The window 24 may block a gap between the inner electrode 21 and the outer electrode 22. The window 24 may be disposed to be exposed to the outside.

An opening 24a that surrounds the hollow body 21b and the inner waterproof ring IO of the inner electrode 21 may be formed in the window 24.

The window 24 may comprise a rear protrusion 24b that surrounds the outer circumference of the hollow body 21b.

The rear protrusion 24b may be formed to be larger than the hollow body 21b. An inner diameter of the rear protrusion 24b may be greater than an outer diameter of the hollow body 21b. A gap may be formed between the rear protrusion 24b and the hollow body 21b.

A fastening hole 24c to which a fastening member C1, such as a screw, for fastening a head PCB 27 to the window 24 may be formed in the rear protrusion 24b.

The fastening member C1 may be fastened to the fastening hole 24c formed in the rear protrusion 24b after passing through a first through hole 27a formed in the head PCB 27, and the LED PCB 26 may be fastened to the window 24.

The receiving portion 24d into which the outer front body 22a of the outer electrode 22 is inserted and accommodated may be formed in the front surface of the window 24.

A portion of the window 24, which is located inside the outer electrode 22, may be an LED area through which light of the LED 25 is transmitted.

The LED 25 may radiate light from a rear of the window 24 to the window 24.

The LED 25 may be installed on a front surface of the LED PCB 26 and may be installed in plural number.

The LED PCB 26 may control and support the plurality of LEDs 25. The LED PCB 26 may be formed in a ring shape.

As shown in FIG. 8, the LED PCB 26 may be accommodated between the hollow body 21b and the rear protrusion 24b.

The front assembly 2 may further comprise the head PCB 27.

Each of the inner electrode 21 and the outer electrode 22 may be electrically connected to the head PCB 27. The LED PCB 26 may be electrically connected to the head PCB 27.

The head PCB 27 may be a kind of Junction PCB, may output a high frequency signal and a microcurrent signal to the inner electrode 21 and the outer electrode 22, output an LED signal to the LED PCB 26, and output a heater signal to the heater H.

In the front assembly 2, the inner electrode 21, the outer electrode 22, the ultrasonic vibrator 23, the heater H, the window 24, and the LED PCB 26 may be placed in front of the head PCB 27.

The ultrasonic vibrator 23 and the heater H may be disposed between the rear surface of the front body 21a of the inner electrode 21 and the front surface of the head PCB 27 in a front-and-rear direction.

The front assembly 2 may further comprise at least one eye care member 28 and 29.

The eye care members 28 and 29 may be connected to the head PCB 27.

The eye care members 28 and 29 may be provided in a plural number. Hereinafter, a pair of eye care members 28 and 29 are described to be provided but the number thereof is not limited thereto.

The pair of eye care members 28 and 29 may be spaced apart from each other. The pair of eye care members 28 and 29 may be spaced apart from each other in a left and right direction Y and may be in contact with the head PCB 27.

The eye care members 28 and 29 may be located on a rear upper side of the inner electrode 21 and the outer electrode 22, and a size of each of the pair of eye care members 28 and 29 may be smaller than the inner electrode 21.

The user may bring at least one of the eye care members 28 and 29 close to a corner of the eye or a side of the nose, and the eye care members 28 and 29 may provide intensive care to a portion that is difficult to reach by the inner electrode 21 or the outer electrode 22.

The front assembly 2 may comprise a front cover 30.

The front cover 30 may be coupled to the first protrusion 12, and the front cover 30 may support the inner electrode 21, the outer electrode 22, the ultrasonic vibrator 23, the heater H, the window 24, the LED PCB 26, the head PCB 27, and the pair of eye care members 28 and 29.

The head PCB 27 may be mounted on the front cover 30.

A front space S2 in which the head PCB 27 and the window 24 are accommodated together may be formed in the front cover 30.

A window receiving portion 40 in which a portion of the window 24 is accommodated may be formed in the front cover 30. The window receiving portion 40 may accommodate the rear protrusion 24b of the window 24 therein.

A front surface of the window 24 may be exposed to the outside and the rear protrusion 24b may be inserted into and accommodated in the window receiving portion 40.

The head PCB 27 may be accommodated with the window 24 in a window receiving portion 40a.

The front space S2 may be formed inside the window receiving portion 40a.

An electrode coupler 40b to which the inner electrode 21 is coupled may be formed on the front cover 30.

The inner electrode 21 may be coupled with the head PCB 27 to the electrode coupler 40b. A fastening member C2, such as a screw, may pass through the electrode coupler 40b formed on the front cover 30 and a second through hole 21d formed in the head PCB 27 and may then fastened to a fastening hole 21d formed in the hollow body 21b of the inner electrode 21 to fasten the inner electrode 21 and the head PCB 27 to the front cover 30.

An outer waterproofing member OR may be disposed between the window 24 and the front cover 30 to prevent moisture or the like from penetrating between the window 24 and the front cover 30.

The outer waterproofing member OR may be an outer waterproof ring disposed between the window receiving portion 40a and the window 24. Hereinafter, the outer waterproof ring is explained using reference numeral OR.

The outer electrode 22 may comprise a rear protrusion 22d that is inserted between the window receiving portion 40a and the window 24 and is located in front of the outer waterproof ring OR. The rear protrusion 22d may function as a stopper in front of the outer waterproof ring OR to prevent arbitrary removal of the outer waterproof ring OR.

Through portions 30A and 30B through which the eye care members 28 and 29 pass may be formed in the front cover 30. The through portions 30A and 30B may be formed on the front cover 30.

The through portions 30A and 30B may be formed as a pair with the same number of the eye care members 28 and 29, and the pair of through portions 30A and 30B may comprise a right through portion 30A through which a right eye care member 29 passes and a left through portion 30B through which a left eye care member 28 passes.

A protrusion 30C protruding upward may be formed on the front cover 30, and the through portions 30A and 30B may be formed in the protrusion 30C.

The through portions 30A and 30B may be connected to the front space S2.

The front cover 30 may comprise a plurality of members, and as shown in FIG. 7, may comprise a main cover 30D in which the front space S2 and the protrusion 30C are formed and a sub cover 30E coupled to a rear surface of the protrusion 30C.

In the intensive care mode, the user may touch the inner electrode 21 and the outer electrode 22 to the face.

In the eye care mode, the user may touch the eye care members 28 and 29 to the face.

As described above, the front assembly 2 may be an absorption promoting head that promotes absorption of cosmetics or medicines.

FIG. 9 is a front view of a heater according to the present embodiment.

The heater H may further comprise a film 50, a heating element 52 formed on the film 50, and a temperature sensor 54 disposed on the film 50.

An example of the film 50 may be a flexible printed circuit board (FPCB).

The heating element 52 may be a heating portion or a heating pattern formed on one side of the film 50.

The temperature sensor 54 may be placed in contact with the inner electrode 21.

After current is applied to the heating element 52, the temperature sensor 54 may detect the temperature and transmit a signal corresponding to the detected temperature to the head PCB 27.

When the temperature detected by the temperature sensor 54 is equal to or greater than a setting value, a controller of the beauty equipment may block the current applied to the heating element 52.

FIG. 10 is a cross-sectional view of an eye care member according to the embodiment.

The pair of eye care members 28 and 29 shown in FIG. 7 may have the same structure, and one eye care member will be described below.

The eye care member may comprise a ball 28a and a terminal 28b.

The ball 28a may be exposed to the outside of the front cover 30 when the eye care member is in contact with the main PCB 27.

The terminal 28b may protrude from the ball 28a and may pass through the through portions 30A and 30B.

The through portions 30A and 30B may comprise a ball accommodator 30F that is rounded and in which the ball 28a is accommodated, and an opening 30F formed in a lower portion of the ball accommodator 30F and through which the terminal 28b passes.

An eye care waterproof ring 60 for sealing a space between the through portions 30A and 30B and the eye care members 28 and 29 may be disposed on the eye care member.

The eye care waterproof ring 60 may be accommodated in a groove 28c formed in the terminal 28b and may be in contact with the through portions 30A and 30B.

The eye care waterproof ring 60 may prevent moisture from penetrating between the eye care members 28 and 29 and the through portions 30A and 30B.

FIG. 11 is an exploded perspective view of a rear assembly according to the present embodiment.

The rear assembly 3 may be a rear head located approximately at an upper rear side of the beauty equipment.

The rear assembly 3 may comprise the thermoelectric element 31 and a cooling cover 32 cooled by the thermoelectric element 31. The rear assembly 3 may comprise a rear cover 33 and the heat sink 34.

The thermoelectric element 31 may cool the cooling cover 32 in front of the cooling cover 32. The rear surface of the thermoelectric element 31 may be in surface contact with the cooling cover 32.

The cooling cover 32 may be coupled to the rear cover 33 and may be disposed to be exposed to the outside. In the cooling care mode, the user may touch the cooling cover 32 to the face.

The cooling cover 32 may be a SUS head made of a SUS material.

The cooling cover 32 may comprise a disk portion 32A in contact with the thermoelectric element 31 and an edge portion 32B that protrudes forward from an edge of the disk portion 32A and surrounds an outer circumference of the rear cover 33.

An insertion space S4 into which an insertion portion 33A of the rear cover 33 is inserted may be formed in the cooling cover 32.

The rear cover 33 may be coupled to the second protrusion 12. The thermoelectric element 31 may be disposed on the rear cover 33, and the rear cover 33 may support the cooling cover 33.

The insertion portion 33A inserted into the insertion space S4 may be formed at a rear side of the rear cover 33. A fastener 33B fastened to the second protrusion 13 may be formed at a front side of the rear cover 33. A receiving portion 33C in which the thermoelectric element 31 is accommodated may be formed on the rear cover 33.

The heat sink 34 may be coupled to the rear cover 33 to dissipate heat from the thermoelectric element 31. The heat sink 34 may be accommodated in the space S1 formed inside the head housing 17.

As described above, the rear assembly 3 may function as a cooling head.

The rear assembly 3 may control the temperature of the cooling cover 32 in multiple stages. For example, stage 1 may be 13° C., stage 2 may be 10° C., and stage 3 may be 5° C.

Depending on the number of times the user inputs the level selection button 11E (refer to FIG. 3), the user may set the temperature of the cooling cover 32 (i.e., the intensity/level of the cooling mode) in multiple stages, and the beauty equipment may control the thermoelectric element 31 according to a setting level.

FIG. 12 is a diagram showing a base according to the present embodiment.

In the main body 1, a charging port 10A for charging the battery 8 and a speaker unit (not shown) for voice guidance when using beauty equipment may be disposed.

The charging port 10A and the speaker unit may be disposed inside the handle 11.

The charging port 10A and the speaker unit may be disposed on the base 15.

A charging hole 15A connected to the inside of the charging port 10A may be formed in the base 15. A speaker hole 15B surrounding a speaker unit 10B may be formed in the base 15.

When the beauty equipment is used, a high frequency may increase deep heat inside the skin, vibration by ultrasonic waves may generate cavitation (cracks between tissues) in the skin, microcurrent may reduce keratin impedance due to a polarity change and stimulate the skin, and iontophoresis by galvanic current may improve a penetration rate of negatively charged substances.

Deep heat caused by output of a high frequency penetrates into the keratin, epidermis, dermis and subcutaneous fat, vibrations caused by ultrasonic waves are transmitted to the keratin, epidermis and dermis, and positive (+) microcurrent and negative (−) microcurrent penetrate into the keratin, epidermis and dermis, and the galvanic current penetrates into the keratin and epidermis.

As described above, deep heat of the skin may be increased, cavitation may be generated, and the skin may be stimulated by a high frequency, ultrasonic waves, and microcurrent, and then when galvanic current is applied, a penetration rate of a negatively charged material contained in cosmetics or the like may be improved.

The above description is merely illustrative of the technical idea of the present disclosure. Those of ordinary skill in the art to which the present disclosure pertains will be able to make various modifications and variations without departing from the essential characteristics of the present disclosure.

Therefore, embodiments disclosed in the present disclosure are not intended to limit the technical idea of the present disclosure, but to describe, and the scope of the technical idea of the present disclosure is not limited by such embodiments.

The scope of protection of the present disclosure should be interpreted by the claims below, and all technical ideas within the scope equivalent thereto should be construed as being comprised in the scope of the present disclosure.

What is claimed:

1. Beauty equipment comprising:
an ultrasonic vibrator configured to generate ultrasonic waves;
an inner electrode with a space in which the ultrasonic vibrator is accommodated;
a window disposed outside an outer circumference of the inner electrode;
a light emitting diode (LED) printed circuit board (PCB) disposed behind the window and having an LED disposed thereon; and
an outer electrode spaced apart from the inner electrode on the window,
wherein the inner electrode comprises:
a front body having a rear surface on which the ultrasonic vibrator is disposed; and
a hollow body protruding rearward from an outer circumference of the front body and having the space formed therein; and
wherein an inner waterproof ring is disposed between the hollow body and the window,
wherein a groove facing the window is formed on an outer circumference of the hollow body; and
wherein the inner waterproof ring is accommodated in the groove.

2. The beauty equipment of claim 1, further comprising a heater disposed on the rear surface of the front body,
wherein the heater is accommodated in the space together with the ultrasonic vibrator and is spaced apart from the ultrasonic vibrator.

3. The beauty equipment of claim 2, wherein the heater further comprises:
a film;
a heating element formed on the film; and
a temperature sensor disposed on the film.

4. Beauty equipment comprising:
an ultrasonic vibrator configured to generate ultrasonic waves;
an inner electrode with a space in which the ultrasonic vibrator is accommodated;
a window disposed outside an outer circumference of the inner electrode;
a light emitting diode (LED) printed circuit board (PCB) disposed behind the window and having an LED disposed thereon; and
an outer electrode spaced apart from the inner electrode on the window,
wherein the inner electrode comprises:
a front body having a rear surface on which the ultrasonic vibrator is disposed; and
a hollow body protruding rearward from an outer circumference of the front body and having the space formed therein; and
wherein an inner waterproof ring is disposed between the hollow body and the window,
wherein the window comprises a rear protrusion surrounding an outer circumference of the hollow body; and
wherein the LED PCB is accommodated between the hollow body and the rear protrusion.

5. Beauty equipment comprising:
an ultrasonic vibrator configured to generate ultrasonic waves;
an inner electrode with a space in which the ultrasonic vibrator is accommodated;
a window disposed outside an outer circumference of the inner electrode;
a light emitting diode (LED) printed circuit board (PCB) disposed behind the window and having an LED disposed thereon; and
an outer electrode spaced apart from the inner electrode on the window,
wherein the inner electrode comprises:
a front body having a rear surface on which the ultrasonic vibrator is disposed; and
a hollow body protruding rearward from an outer circumference of the front body and having the space formed therein; and
wherein an inner waterproof ring is disposed between the hollow body and the window,
the beauty equipment further comprises:
a front cover formed with an electrode coupler to which the inner electrode is coupled; and a window receiving portion that accommodates a portion of the window,
wherein an outer waterproof ring is disposed between the window receiving portion and the window.

6. The beauty equipment of claim 5, wherein the outer electrode comprises a rear protrusion inserted between the window receiving portion and the window and disposed in front of the outer waterproof ring.

7. Beauty equipment comprising:
an ultrasonic vibrator configured to generate ultrasonic waves;
an inner electrode with a space in which the ultrasonic vibrator is accommodated;
a window disposed outside an outer circumference of the inner electrode;
a light emitting diode (LED) printed circuit board (PCB) disposed behind the window and having an LED disposed thereon; and
an outer electrode spaced apart from the inner electrode on the window,
wherein the inner electrode comprises:
a front body having a rear surface on which the ultrasonic vibrator is disposed; and
a hollow body protruding rearward from an outer circumference of the front body and having the space formed therein; and
wherein an inner waterproof ring is disposed between the hollow body and the window,
the beauty equipment further comprises:
a head PCB to which each of the inner electrode and the outer electrode is connected; and
an eye care member connected to the head PCB.

8. The beauty equipment of claim 7, further comprising:
a front cover with a through portion through which the eye care member passes,
wherein an eye care waterproof ring is disposed on the eye care member and is configured to seal a space between the through portion and the eye care member.

9. The beauty equipment of claim 8, wherein the eye care member comprises:
a ball exposed outside the front cover; and
a terminal protruding from the ball and passing through the through portion; and wherein the eye care waterproof ring is accommodated in a groove formed in the terminal and is in contact with the through portion.

* * * * *